Figure 1:
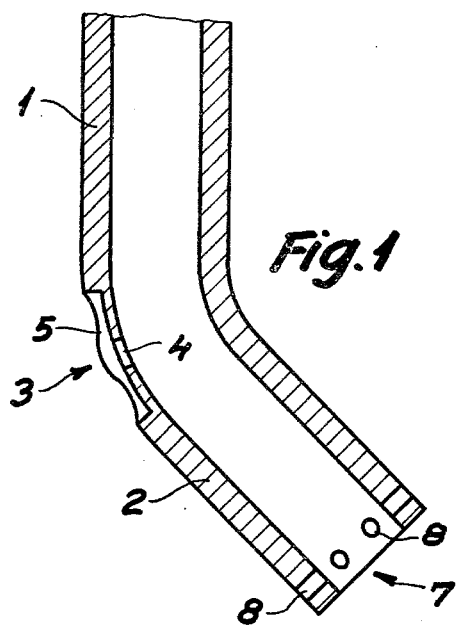

United States Patent [19]

Lomholt

[11] 4,227,529
[45] Oct. 14, 1980

[54] TRACHEAL SUCTION CATHETER
[75] Inventor: Vagn N. F. Lomholt, Gentofte, Denmark
[73] Assignee: Molnlycke Steritex A/S, Espergaerde, Denmark
[21] Appl. No.: 4,354
[22] Filed: Jan. 18, 1979
[30] Foreign Application Priority Data
Jan. 23, 1978 [DK] Denmark .................. 325/78
[51] Int. Cl.³ .................. A61M 25/00; A61M 1/00
[52] U.S. Cl. .................. 128/276; 128/350 R; 433/96
[58] Field of Search .................. 128/208, 276–278, 128/348–351, 200.26, 207.14; 433/91, 96

[56] References Cited

U.S. PATENT DOCUMENTS

| | | | |
|---|---|---|---|
| 3,175,557 | 3/1965 | Hammond | 128/276 X |
| 3,945,385 | 3/1976 | Sackner | 128/276 X |
| 3,965,901 | 6/1976 | Penny et al. | 128/350 R |
| 4,037,605 | 7/1977 | Firth | 128/351 |

FOREIGN PATENT DOCUMENTS 1248230  8/1967  Fed. Rep. of Germany .......... 128/351

*Primary Examiner*—Dalton L. Truluck
*Attorney, Agent, or Firm*—Watson, Leavenworth, Kelton & Taggart

[57] ABSTRACT

The invention relates to a tracheal suction catheter comprising a flexible tube whose outermost portion has a side bend forming a knee on the tube, an aperture being provided in the tube wall adjacent the knee.

The object of the invention is to provide a construction reducing as much as possible the risk of the catheter being clamped to the mucosa, and according to the invention this is achieved by the tube wall immediately around said aperture being sunk with respect to the cylindrical surface of the tube. Suction from the mucosa is thus spread over a greater area, and the aperture itself is spaced from the mucosa ensuring that the mucosa is not damaged, neither during insertion nor during suction.

1 Claim, 2 Drawing Figures

U.S. Patent  Oct. 14, 1980  4,227,529

TRACHEAL SUCTION CATHETER

The invention relates to a tracheal suction catheter of the type comprising a flexible, externally smooth tube whose outermost free end is open, the outermost portion of said tube being formed with a side bend, an aperture being provided immediately adjacent the knee formed by said side bend. It has been found that apertures in the wall of the tube often give rise to considerable damage to the mucosa during insertion and suction because the tube is clamped thereto upon application of suction and only exerts the sucking function on a very limited area, having an ineffective suction of mucosa in its wake. The object of the invention is to provide a tracheal suction catheter which is particularly effective and prevents damage to the mucosa.

This is achieved according to the invention by forming a tracheal suction catheter of said type such that immediately around said aperture the tube wall is sunk with respect to the cylindrical surface of the tube. This means that the catheter will not have such a local suction as the known catheters because the aperture is spaced from the mucosa, resulting in a spreading of suction over a larger area. This also ensures that the mucosa are not damaged, neither during insertion nor during suction.

It is common knowledge in the art to provide a tracheal suction catheter with several apertures as it may happen that an aperture is clogged by mucus. In a catheter of the subject type it has been found that a particularly effective suction may be obtained by providing said catheter with a plurality of small apertures in the tube wall immediately adjacent the free, open end of the tube, the size of the aperture at the knee and the size and/or number of said small apertures at the tube end being mutually adapted so as to obtain a substantially equally vigorous suction at the tube end and at the knee. The small apertures at the tube end also cause the suction zone to be expediently spread at the open tube end so that the mucosa will not be damaged there either.

Figure 2:
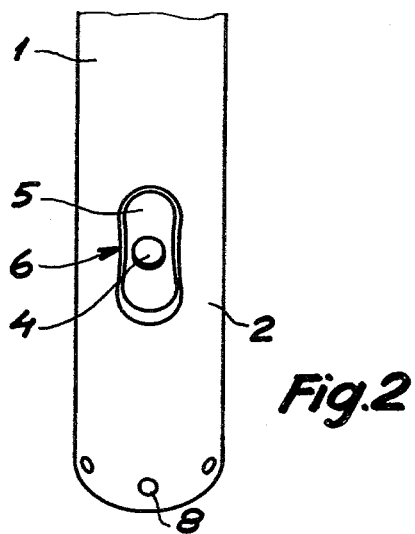

The invention will be described in more detail below with reference to the drawing, in which FIG. 1 shows the lower end of a preferred embodiment of a tracheal suction catheter in longitudinal section, and FIG. 2 is a side view of the same catheter.

FIG. 1 shows the lower end of a tracheal suction catheter comprising an externally smooth tube 1 whose lower portion has a side bend 2, resulting in the formation of a knee 3. At the knee 3 there is formed an aperture 4 and the portion of the tube wall defining said aperture has a sunk area 5. As will be seen in FIG. 2 the sunk area is formed so as to extend a considerable distance longitudinally of the tube at both sides of the aperture 4, while the sunk area 5 immediately opposite the aperture 4 tapers inwardly as at 6. Said taper may extend adjacent the aperture, but leaves preferably some sunk area all round said aperture.

The tube 1 is open at the free end as indicated at 7, and adjacent thereto the tube wall is provided with a plurality of small apertures 8 whose size and number are adapted with respect to the aperture 4 so as to obtain essentially the same suction effect at the tube end as at the knee 3.

I claim:

1. In a tracheal suction catheter of the type comprising a flexible, externally smooth tube whose outermost free end is open and is provided with a plurality of small apertures in the tube wall immediately adjacent the free, open end of the tube, the outermost portion of said tube being further formed with a side bend, there being a further aperture in said tube wall immediately adjacent the knee formed by said side bend, the provision of a depression in the outer surface of the wall portion surrounding said further aperture, the size of the further aperture and the size and number of said small apertures being related such as to obtain a substantially equal degree of suction force at the tube end and at the knee.

* * * * *